US011142567B2

(12) United States Patent
Yeh et al.

(10) Patent No.: US 11,142,567 B2
(45) Date of Patent: Oct. 12, 2021

(54) ANTI-DENGUE VIRUS ANTIBODY, PHARMACEUTICAL COMPOSITION COMPRISING THE SAME, AND USES THEREOF

(71) Applicants: NATIONAL CHENG KUNG UNIVERSITY, Tainan (TW); DCB-USA LLC, Wilmington, DE (US)

(72) Inventors: Trai-Ming Yeh, Tainan (TW); Yung-Chun Chuang, Hsinchu (TW); Yen-Chung Lai, Taipei (TW)

(73) Assignees: NATIONAL CHENG KUNG UNIVERSITY, Tainan (TW); DCB-USA LLC, Wilmington, DE (US)

( * ) Notice: Subject to any disclaimer, the term of this patent is extended or adjusted under 35 U.S.C. 154(b) by 0 days.

(21) Appl. No.: 16/616,416

(22) PCT Filed: May 22, 2018

(86) PCT No.: PCT/US2018/033776
§ 371 (c)(1),
(2) Date: Nov. 22, 2019

(87) PCT Pub. No.: WO2018/217681
PCT Pub. Date: Nov. 29, 2018

(65) Prior Publication Data

US 2020/0087383 A1 Mar. 19, 2020

Related U.S. Application Data

(60) Provisional application No. 62/509,205, filed on May 22, 2017.

(51) Int. Cl.

| | |
|---|---|
| ***A61P 31/14*** | (2006.01) |
| ***A61K 39/42*** | (2006.01) |
| ***C07K 16/10*** | (2006.01) |
| *A61K 39/00* | (2006.01) |
| *A61K 39/12* | (2006.01) |

(52) U.S. Cl.
CPC .......... *C07K 16/1081* (2013.01); *A61K 39/42* (2013.01); *A61P 31/14* (2018.01); *A61K 39/12* (2013.01); *A61K 2039/505* (2013.01); *A61K 2039/545* (2013.01); *C07K 2317/33* (2013.01); *C07K 2317/734* (2013.01); *C07K 2317/76* (2013.01)

(58) Field of Classification Search
None
See application file for complete search history.

(56) References Cited

U.S. PATENT DOCUMENTS

2007/0134256 A1* 6/2007 Lai .................... C07K 16/1081 424/159.1

OTHER PUBLICATIONS

Chuang et al., Dengue Virus Nonstructural Protein 1-Induced Antibodies Cross-React with Human Plasminogen and Enhance Its Activation, 2016 (Epub Dec. 28, 2015), Journal of Immunology, vol. 196, pp. 1218-1226.*

* cited by examiner

*Primary Examiner* — Benjamin P Blumel

(57) ABSTRACT

Disclosed herein is an anti-DENV antibody, a pharmaceutical composition comprising the same, and uses thereof. According to embodiments of the present disclosure, the anti-DENV antibody comprises a heavy chain variable region and a light chain variable region, in which the heavy chain variable region comprises amino acid sequences of SEQ ID NOs: 1-3, and the light chain variable region comprises amino acid sequences of SEQ ID NOs: 5-7.

8 Claims, 11 Drawing Sheets

Specification includes a Sequence Listing.

ANTI-DENGUE VIRUS ANTIBODY, PHARMACEUTICAL COMPOSITION COMPRISING THE SAME, AND USES THEREOF

CROSS-REFERENCE TO RELATED APPLICATIONS

This application relates to and claims the benefit of U.S. Provisional Application No. 62/509,205, filed May 22, 2017; the content of the application is incorporated herein by reference in its entirety.

BACKGROUND OF THE INVENTION

1. Field of the Invention

The present disclosure in general relates to the field of treating viral infection. More particularly, the present disclosure relates to an antibody and its applications in the treatment of dengue virus (DENV) infection.

2. Description of Related Art

Dengue virus (DENV), a mosquito-borne single positive-stranded RNA virus of the family Flaviviridae and genus Flavivirus, exists as five serotypes (DENV serotypes 1-5, the fifth is reported in 2013) and is closely related to other flaviviruses, such as yellow fever and tick-borne encephalitis viruses. In addition to fatigue, nausea, vomiting, fever, headache, and joint and muscular pain, DENV infection may cause life-threatening dengue hemorrhagic fever (DHF) and dengue shock syndrome (DSS). There are several vaccine candidates in clinical trials, including a licensed tetravalent dengue vaccine, which was developed by the company Sanofi Pasteur. However, the therapeutic drugs are still highly desirable to cure the acute dengue disease before popularization of dengue vaccine.

Nowadays, the anti-DENV agent and the host modulator are the main therapeutic approaches for the treatment of DENV infection. The anti-DENV agents directly targeting the molecule of DENV include, nucleoside analogue (e.g., R1479), protease inhibitor (e.g., α-ketoamide, BP13944 and retrocyclin 1), capsid inhibitor (e.g., ST-148), and viral peptide inhibitor (e.g., DN59). The host modulator focuses on the host factors thereby blocking the replication and infection in the host cells. This type of agent includes guanosine analogue (e.g., ribavirin), IMP dehydrogenase inhibitor (e.g., mycophenolic acid), α-glucosidase inhibitor (e.g., castanospermine, deoxynojirimycin and cyclosporine), inhibitor of 3-hydroxy-3-methylglutaryl coenzyme A (HMG-CoA) reductase (e.g., lovastatin), and host kinase inhibitor (e.g., AZD0530 and dasatinib). However, each of the therapeutic approaches listed above has its limitation, such as high-cost, low efficiency, and/or side effect.

Nonstructural protein 1 (NS1) of DENV has been proposed to act as a viral toxin, which enhances vascular permeability and disturbs coagulation system. Further, it also plays a role in the viral replication, pathogenesis and immune evasion of DENV. Several strategies of NS1 inhibition by anti-NS1 antibodies have thus been documented in the past decades. Nevertheless, autoantibodies elicited from molecular mimicry of NS1 to host proteins hinders the development of NS1-based antibody drugs. According to the previous reports, in addition to the NS1 protein, the anti-NS-1 antibody also reacts with the host cells (e.g., endothelial cells, liver cells, platelets and thrombocytes) and coagulation factors (e.g., plasminogen and thrombin) that then activates the cells/factors and causes the cell death by apoptosis or complement-mediated lysis.

In view of the foregoing, there exists in the related art a need for a novel therapeutic agent for safely and efficiently protecting and/or treating the acute DENV infection a subject.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to an antibody or a fragment thereof. The present antibody comprises a heavy chain variable region and a light chain variable region, in which the heavy chain variable region comprises the amino acid sequences of SEQ ID NOs: 1-3, and the light chain variable region comprises the amino acid sequences of SEQ ID NOs: 5-7.

According to some embodiments of the present disclosure, the heavy chain variable region has an amino acid sequence at least 85% identical to the sequence of SEQ ID NO: 4, and the light chain variable region has an amino acid sequence at least 85% identical to the sequence of SEQ ID NO: 8. According to one working example of the present disclosure, the heavy chain variable region has the amino acid sequence of SEQ ID NO: 4, and the light chain variable region has the amino acid sequence of SEQ ID NO: 8.

The second aspect of the present disclosure is directed to a pharmaceutical composition for the treatment of a DENV infection. The present pharmaceutical composition comprises the present antibody, and a pharmaceutically acceptable carrier.

Another aspect of the present disclosure pertains to a method of treating a DENV infection in a subject. According to embodiments of the present disclosure, the method comprises administering to the subject an effective amount of the present antibody.

According to certain embodiments of the present disclosure, the subject is a human. In these embodiments, the effective amount is about 1 μg/Kg to 100 mg/Kg. Preferably, the effective amount is about 10 μg/Kg to 10 mg/Kg. More preferably, the effective amount is about 0.1 mg/Kg to 1 mg/Kg.

In general, the DENV is DENV serotype 1, 2, 3 or 4.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 5A: the present anti-DENV antibody 33D2 reduces the titer of DENV serotype 2. FIG. 5B: the present anti-DENV antibody 33D2 reduces the titer of DENV serotype 2 in a dose-dependent manner. FIG. 5C: the present anti-DENV antibody 33D2 reduces the titer of DENV serotype 1 (panel A), serotype 2 (panel B), serotype 3 (panel C) and serotype 4 (panel D) in a dose-dependent manner according to another embodiment of the present disclosure;

DETAILED DESCRIPTION OF THE INVENTION

Figure 1:
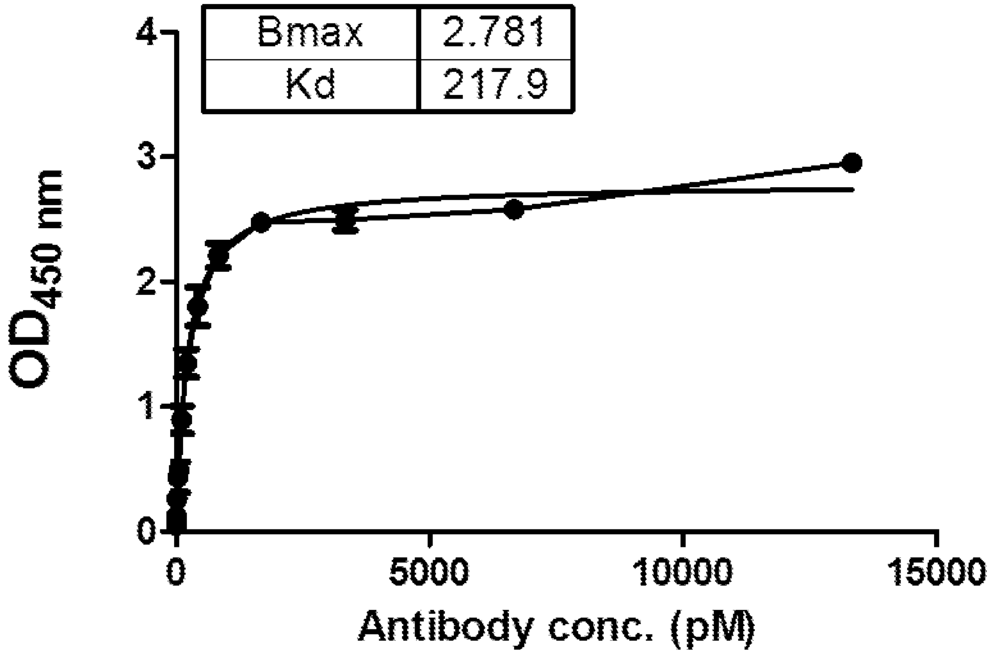
FIG. 1 is a line chart depicting the binding affinity between the present anti-DENV antibody 33D2 and the NS1 protein according to another embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antigen," unless indicated otherwise, refers to any agent that, when introduced into an immunocompetent human or animal, stimulates a humoral and/or cellular immune response. The antigen may be a pure substance, a mixture of substances, or particulate material (including cells, cell fragments, or cell derived fragments) or a live, usually attenuated, organism or virus. Examples of suitable antigens include, but are not limited to, a protein, glycoprotein, lipoprotein, polypeptide, peptide, carbohydrate/polysaccharide, lipopolysaccharide, toxin, virus, bacterium, fungus, and parasite.

The term "antibody" as used herein refers to an immunoglobulin molecule which is able to specifically bind to a specific epitope on an antigen. Antibodies can be intact immunoglobulins derived from natural sources or from recombinant sources, and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment. The antibody fragment in the present invention may exist in a variety of forms including, for example, variable fragment (Fv), single-chain variable fragment (scFv), antigen-binding fragment (Fab) and $F(ab)_2$, as well as single chain antibodies.

The term "monoclonal antibody" or "mAb" as used herein refers to an antibody obtained from a population of substantially homogeneous antibodies, and is not to be constructed as requiring production of the antibody by any particular method. In contrast to polyclonal antibodies, which typically include different antibodies directed to different epitopes, each monoclonal antibody is directed against a single determinant (i.e., epitope) on the antigen. The monoclonal antibodies of the present disclosure may be made by hybridoma method or by recombinant DNA methods. The monoclonal antibodies herein specifically include "chimeric" or "recombinant" antibodies, in which a portion of the heavy and/or light chain is identical with or homologous to corresponding sequences in antibodies derived from a particular species or belonging to a antibody class or subclass, while the remainder of the chain identical with or homogolous to corresponding sequences in antibodies derived from another species or belonging to another antibody class or subclass, as well as fragments of such antibodies, as long as they exhibit the desired biological activity.

The term "complementarity determining region" or "CDR" used herein refers to the hypervariable region of an antibody molecule that forms a surface complementary to the three-dimensional surface of a bound antigen. Proceeding from N-terminus to C-terminus, each of the antibody heavy and light chains comprises three CDRs (CDR 1, CDR 2 and CDR3). An antigen combining site, therefore, includes a total of six CDRs that comprise three CDRs from the variable region of a heavy chain (i.e., CDR-H1, CDR-H2 and CDR-H3) and three CDRs from the variable region of a light chain (i.e., CDR-L1, CDR-L2 and CDR-L3). The amino acid residues of CDRs are in close contact with bound antigen, wherein the closest antigen contact is usually associated with the heavy chain CDR3.

The "variable region" or "variable domain" of an antibody refers to the amino-terminal domains of heavy or light chain of the antibody. These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three CDRs or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (x) and lambda (k), based on the amino acid sequences of their constant domains.

As discussed herein, minor variations in the amino acid sequences of antibodies are contemplated as being encompassed by the presently disclosed and claimed inventive concept(s), providing that the variations in the amino acid sequence maintain at least 85% sequence identity, such as at least 85%, 86%, 87%, 88%, 89%, 90%, 91%, 92%, 93%, 94%, 95%, 96%, 97%, 98% and 99% sequence identity. The present antibody may be modified specifically to alter a feature of the antibody unrelated to its physiological activity. For example, certain amino acids can be changed and/or deleted without affecting the physiological activity of the antibody in this study (i.e., its ability to treat dengue virus infection). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional antibody can readily be determined by assaying the specific activity of the antibody derivative. Fragments or analogs of antibodies can be readily prepared by those of ordinary skill in the art. Preferred amino- and carboxy-termini of fragments or analogs occur near boundaries of functional domains. In one example, one amino acid residue (e.g., valine) of the present antibody is conservatively replaced (e.g., by leucine). In other examples, two amino acid residues of the present antibody are conservatively replaced by other suitable amino acid residues, for example, valine (V) and arginine (R) are replaced by the pair of amino acids that includes, but is not limited to, methionine (M) and lysine (K), lysine (K) and proline (P), tryptophan (W) and isoleucine (I), isoleucine (I) and proline (P), asparagine (N) and valine (V), and glutamine (G) and lysine (K).

"Percentage (%) sequence identity" is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100$$

where X is the number of amino acid residues scored as identical matches by the sequence alignment program BLAST in that program's alignment of A and B, and where Y is the total number of amino acid residues in A or B, whichever is shorter.

As used herein, the term "treat," "treating" and "treatment" are interchangeable, and encompasses partially or completely preventing, ameliorating, mitigating and/or managing a symptom, a secondary disorder or a condition associated with DENV infection, in which inhibiting DENV replication and/or reducing the viral titer provide a benefit to the subject having or suspected of having such symptom, disorder or condition. The term "treating" as used herein refers to application or administration of one or more antibodies of the present disclosure to a subject, who has a symptom, a secondary disorder or a condition associated with DENV infection, with the purpose to partially or completely alleviate, ameliorate, relieve, delay onset of, inhibit progression of, reduce severity of, and/or reduce incidence of one or more symptoms, secondary disorders or features associated with DENV infection. Symptoms, secondary disorders, and/or conditions associated with DENV infection include, but are not limited to, fatigue, nausea, vomiting, fever, headache, joint and muscular pain, DHF and DSS. Treatment may be administered to a subject who exhibits only early signs of such symptoms, disorder, and/or condition for the purpose of decreasing the risk of developing the symptoms, secondary disorders, and/or conditions associated with DENV infection. Treatment is generally "effective" if one or more symptoms or clinical markers are reduced as that term is defined herein. Alternatively, a treatment is "effective" if the progression of a symptom, disorder or condition is reduced or halted.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the antibody of the present disclosure), such as molar concentration, mass concentration, volume concentration, molality, mole fraction, mass fraction and mixing ratio. Specifically, the term "therapeutically effective amount" used in connection with the antibody described herein refers to the quantity of the antibody, which is sufficient to alleviate or ameliorate the symptoms associated with the cancer in the subject. Persons having ordinary skills could calculate the human equivalent dose (HED) for the medicament (such as the present antibody) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" refers to a mammal including the human species that is treatable with methods of the present invention. The term "subject" is intended to refer to both the male and female gender unless one gender is specifically indicated.

2. Description of the Embodiments

(i) Anti-DENV Antibody

The first aspect of the present disclosure is directed to an antibody, which is capable of recognizing DENV-infected cells and inhibit virus propagation. The present antibody comprises a heavy chain variable region and a light chain variable region, each of which comprises three CDRs. According to embodiments of the present disclosure, the CDRs of the heavy chain variable region (i.e., CDR-1, CDR-2 and CDR-3 of the heavy chain variable region) respectively comprises the amino acid sequences of SEQ ID NOs: 1-3; and the CDRs of the light chain variable region (i.e., CDR-1, CDR-2 and CDR-3 of the light chain variable region) respectively comprises the amino acid sequences of SEQ ID NOs: 5-7.

According to some embodiment of the present disclosure, the heavy chain variable region has an amino acid sequence at least 85% (e.g., 85%, 86%, 87%, 88%, 89%, 90%, 91%, 92%, 93%, 94%, 95%, 96%, 97%, 98%, 99% or 100%) identical to the sequence of SEQ ID NO: 4, and the light chain variable region has an amino acid sequence at least 85% (e.g., 85%, 86%, 87%, 88%, 89%, 90%, 91%, 92%, 93%, 94%, 95%, 96%, 97%, 98%, 99% or 100%) identical to the sequence of SEQ ID NO: 8. Preferably, the heavy chain variable region has an amino acid sequence at least 90% identical to the sequence of SEQ ID NO: 4, and the light chain variable region has an amino acid sequence at least 90% identical to the sequence of SEQ ID NO: 8. More preferably, the heavy chain variable region has an amino acid sequence at least 95% identical to the sequence of SEQ ID NO: 4, and the light chain variable region has an amino acid sequence at least 95% identical to the sequence of SEQ ID NO: 8. According to one working example of the present disclosure, the heavy chain variable region has the amino acid sequence of SEQ ID NO: 4, and the light chain variable region has the amino acid sequence of SEQ ID NO: 8.

To produce the desired monoclonal antibodies, animals such as mice, rats or rabbits are first immunized with a suitable antigen at a suitable dose. Generally, adjuvant and the suitable antigen are mixed together when immunizing the animals with suitable antigen. According to one working example of the present disclosure, the antigen useful in producing the present monoclonal antibody (i.e., mAb 33D2) comprises the amino acid sequence of SEQ ID NO: 11 or 12). According to the preferred example of the present disclosure, the animals are immunized with the antigen (i.e., DENV NS1 antigen) comprising the amino acid sequence of SEQ ID NO: 11 so as to produce anti-DENV antibodies, and the present mAb 33D2 is then selected in vitro therefrom by the antigen comprising the amino acid sequence of SEQ ID NO: 12. Examples of adjuvants useful for this invention include Freund's complete adjuvant (FCA), Freund's incomplete adjuvant (FIA), and aluminum hydroxide adjuvant. Immunization is generally carried out mainly by intravenous, subcutaneous, intraperitoneal or intramuscular injection of the antigen. The immunization interval is not particularly limited. Immunization may be carried out at intervals of several days to several weeks, preferably 2 to 3 weeks, for 1 to 10 times, preferably 2 to 5 times. Once antibody titers reaches 2 or more in the absorbance level as the result of immunization, the animals are left for about 1 month. Then, re-immunization is carried out for at least once, preferably 3 to 4 times. Several days, preferably 3 to 5 days, after the final immunization, splenic cells and regional lymph nodes are removed. Blood samples are taken regularly after immunization and subject to centrifugation to separate sera. The resultant sera are then subject to measurement of antibody titers by any suitable method, which includes, and is not limited to, enzyme linked immunosorbent assay (ELISA), enzyme immunoassay (EIA), or radio immunoassay (MA). In one preferred example, antibody titers are measured by ELISA. Then, final immunization is given to those animals showing high antibody titers to the antigen.

Antibody-producing cells are prepared from splenic cells and regional lymph nodes or the like of the immunized animals. In the preparation of antibody-producing cells, it is preferably to remove tissue debris and erythrocytes as much as possible. Commercial erythrocyte remover may be used to this purpose. Alternatively, a buffer ammonium chloride and Tris may be prepared and used. The thus prepared antibody-producing cells are immediately fused with immortal cells such as myeloma cells to produce hybridoma cells, which semi-eternally continue to proliferate while producing antibodies. Commonly available cell strain derived from an animal such as mouse may be used. A preferable cell strain to be used in this invention should be those that fuse efficiently, support stable high level production of antibody and are sensitive to HAT selection medium, which contains hypoxanthine, thymidine and aminopterin, and should survive there only when fused with antibody-producing cells. Examples of myeloma cells include, but are not limited to, mouse myeloma cell line (such as myeloma FO cells) and human myeloma cell line (such as Karpas 707H).

Cell fusion is usually carried out by mixing splenic cells or lymph node cells with a commercial available myeloma cells in the presence of a cell-fusion promoter, such as polyethylene glycol (PEG) having an average molecular weight from about 200 to 20,000 daltons or the like. Alternatively, cell fusion may be carried out in a commercial cell fusion device utilizing electric stimulation such as electrofusion. After the fusion, the resultant cells are then diluted and cultured in HAT medium.

Hybridomas of interest are then selected from the fused cells. The fused cells surviving cultured in HAT medium would form colonies. The supernatant of each culture well is then collected and examined for the presence or absence of antibody titers to the antigen. As a method of confirmation, ELISA, EIA or RIA may be used, in which antigen is coated onto the plates and used as a screening criteria. Once antibody-positive wells are identified, cells are then cultured in a HT medium, which does not contain aminopterin. After culturing for a while, antibody titers in the culture supernatant are confirmed again. Cells that are finally selected are then subject to cloning to obtain single cells. Clones that exhibit high specificity to the antigen are selected, and are proliferated to some extent to establish hybridomas.

According to preferred embodiments of the present disclosure, one hybridoma is selected, and the monoclonal antibody (e.g., mAb 33D2) may be isolated or prepared therefrom by any known method. For example, the antibody may be prepared from cultured supernatant obtained by culturing hybridoma in a medium with low serum concentration. Alternatively, hybridoma may be injected into abdominal cavities of animals and the resultant abdominal dropsies are collected to prepare the antibody. The antibody may be purified or isolated by methods that employ affinity column, gel filtration chromatography, ion exchange chromatography or the like. Any of these known methods may be appropriately selected or used in combination.

Alternatively, the present antibody may be produced by DNA cloning or DNA synthesis. DNA encoding the present antibody may be easily isolated and sequenced by use of conventional procedures, such as using oligonucleotide probes that are capable of binding specifically to genes encoding the heavy and light chains of the monoclonal antibodies. The hybridoma cell serves as a preferred source of such DNA. Once isolated, the DNA may be placed into expression vectors, which are then transfected into host cells such as *E. Coli* cells, simian COS cells or Chinese hamster ovary (CHO) cells or myeloma cells that do not produce immunoglobulin proteins, to synthesize the desired monoclonal antibodies in the recombinant host cells.

According to one working example of the present disclosure, the DNA encoding the present monoclonal antibody (i.e., mAb 33D2) comprises two polynucleotide sequences respectively corresponding to the heavy chain variable region and the light chain variable region of the present monoclonal antibody. In the example, the first polynucleotide sequences comprises the sequence of SEQ ID NO: 9, and the second polynucleotide sequences comprises the sequence of SEQ ID NO: 10. According to the example, the CDR-H1, CDR-H2 and CDR-H3 are respectively encoded by the polynucleotide sequences of SEQ ID NOs: 13-15, and the CDR-L1, CDR-L2 and CDR-L3 are respectively encoded by the polynucleotide sequences of SEQ ID NOs: 16-18.

The monoclonal antibody thus produced and the DNA encoding such antibody can then be used to produce chimeric antibodies (e.g., bi-specific antibodies), humanized antibodies and/or antibody fragments derived thereof.

In general, the humanized antibody may be produced by CDR grafting, in which the CDR regions in the heavy chain variable region and light chain variable region of a human antibody are replaced with the appropriate CDR coding segments (such as the CDRs respectively having the amino acid sequences of SEQ ID NOs: 1-3 and 5-7). The resulting antibodies therefore have variable regions in which only the CDRs are from the original mouse antibodies, while the framework regions in the heavy chain variable region and light chain variable region as well as the constant region (i.e., CK or CH1-H—CH2-CH3) are those of human IgG.

Depending on desired purposes, the present mAb 33D2 may be in the form of immunoglobulin G (IgG), IgA, IgE, IgD or IgM. According to the preferred embodiments, the present mAb 33D2 is in the form of IgG. In one working example, the present mAb 33D2 is an IgG 2a antibody.

According to certain embodiments of the present disclosure, the present antibody is capable of recognizing DENV-infected cells and inhibit virus propagation, while would not cross react with the protein, cell, tissue or organ of the subject, for example, the host protein, platelet, endothelial cell and coagulation factor. Accordingly, compared with conventional antibodies, the present antibody provides a safer means to protect and/or treat DENV infection in the subject.

According to some embodiments of the present disclosure, the DENV recognized and neutralized by the present antibody is any of DENV serotype 1, 2, 3 or 4.

(ii) Pharmaceutical Composition Comprising the Present Anti-DENV Antibody

The second aspect of the present disclosure is directed to a pharmaceutical composition for the prophylaxis and/or treatment of a DENV virus infection. The present pharmaceutical composition comprises the present antibody according to any of the above-mentioned aspect and embodiments of the present disclosure; and a pharmaceutically acceptable carrier.

Generally, the mAb33D2 of this invention is present at a level of about 0.1% to 99% by weight, based on the total weight of the pharmaceutical composition. In some embodiments, the mAb33D2 of this invention is present at a level of at least 1% by weight, based on the total weight of the pharmaceutical composition. In certain embodiments, the present mAb33D2 is present at a level of at least 5% by weight, based on the total weight of the pharmaceutical composition. In still other embodiments, the present mAb33D2 is present at a level of at least 10% by weight, based on the total weight of the pharmaceutical composition. In still yet other embodiments, the present mAb33D2 is present at a level of at least 25% by weight, based on the total weight of the pharmaceutical composition.

Depending on the desired purpose, the pharmaceutically acceptable carrier may be any of a liquid, gel, cream, ointment, lotion, suspension and emulsion. The composition may be manufactured using carriers prepared according to conventional techniques using, conventional ingredients and agents which are well known in the industry. Other agents which may also be dispersed in the carrier include the following: moisturizers, humectants, anti-dusting agents, emulsifiers, and selected amino acids.

Examples of substances that may serve as pharmaceutically acceptable carriers are gelatin, excipients, pyrogen-free water, isotonic saline, and phosphate buffer solutions. The choice of a pharmaceutically-acceptable carrier to be used in conjunction with an antibody is basically determined by the way the composition is to be administered.

The pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

According to some embodiments, the present composition is parentally administered to the subject in need thereof. To prepare a parental formulation, sterile injectable or suspension are required so as to prevent the recipients from microorganism infections. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

(iii) Method of Treating DENV Infection

Another aspect of the present disclosure pertains to a method of treating a DENV infection in a subject. The method comprises administering to the subject an effective amount of the present antibody or pharmaceutical composition according to any of the above-mentioned aspects and embodiments of the present disclosure.

In general, the effective amount of the antibody or the pharmaceutical composition may vary with many factors, such as the physical condition of the patient (e.g., the patient's body mass, age, or gender), the type of mammal or animal being treated, the duration of the treatment, and the nature of concurrent therapy (if any).

According to one embodiment, the subject is a mouse. To elicit a therapeutic effect in mice, about 12 μg/Kg to 1.2 g/Kg body weight of the present antibody is administered to the subject, such as 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980 or 990 μg/Kg body weight, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1,000, 1,100 or 1,200 mg/Kg body weight. Preferably, the present antibody is administered to the subject in the amount of about 120 μg/Kg to 120 mg/Kg body weight. According to one working example, the present antibody is administered to the subject in the amount of about 1.2-12 mg/Kg body weight.

A skilled artisan could calculate the human equivalent dose (HED) of the present antibody, based on the doses determined from animal models. Accordingly, the effective amount of the present antibody is about 1 μg/Kg to 100 mg/Kg body weight for human, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980 or 990 μg/Kg body weight, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/Kg body weight. Preferably, the effective HED is about 10 μg/Kg to 10 mg/Kg body weight. In one preferred example, the effective HED is about 0.1 mg/Kg to 1 mg/Kg body weight.

Depending on desired effects, the amount may be administered in a single dosage or in multiple dosages in a day, such as in 2, 3, 4 or more dosages per day. Alternatively, the amount may be administered in multiple dosages in multiple days.

The present antibody or the pharmaceutical composition comprising the same can be administered to the subject by any appropriate route, such as transmucosal, subcutaneous, intradermal, intramuscular, intravenous, and intraperitoneal injection. According to one specific example, the present antibody or the pharmaceutical composition comprising the same is intravenously or intraperitoneally injected to the subject.

Basically, the subject treatable by the present method is a mammal, for example, a human, a mouse, a rat, a hamster, a guinea pig, a rabbit, a dog, a cat, a cow, a goat, a sheep, a monkey, and a horse. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Material and Methods

Virus Titration and Fluorescent Focus Assay (FFA)

For virus titration, the fluorescent focus assay was used to determine the virus titer. In brief, supernatants containing infectious virus were collected and stored below −70° C. until use. Supernatant was serially diluted and incubated with BHK-21 cells for 2 hours at 37° C. The monolayers were then overlaid with DMEM containing 2% FBS and 1% methylcellulose and incubated at 37° C. for 2-3 days. Virus foci were stained with anti-NS1 antibody (mAb 33D2) followed by Alexa 488-conjugated goat anti-mouse IgG and visualized with a fluorescence microscope.

Cell Recognition Assay

To evaluate whether the anti-NS1 mAb 33D2 would recognize DENV-infected cells, four serotypes of DENV-infected or mock infected HuH-7 cells were detached with PBS containing 4 mM EDTA and washed with PBS. After staining of mAb 33D2 (10 μg/ml), Alexa 488-conjugated secondary antibody was added. Detection and analysis were performed using a flow cytometer. The quantification was analyzed by a software. The analysis data was depicted in FIG. 2.

Cell Viability and MTT Assay

A total of $8\times10^3$ HuH-7 cells were seeded on 96-well plates. Treated cells were co-incubated with 5 mg/ml MTT stock solution at a 1:10 dilution for another 4 hours. Then, the media were removed followed by the addition of 100 μl DMSO into each well. After the precipitates were dissolved in DMSO for approximately 10 minutes, the absorbance was read at 570 nm. The viability was calculated as [1−(OD control-OD sample)/OD control]×100%.

Enzyme-Linked Immunosorbent Assay (ELISA)

For indirect ELISA, 50 μl of proteins (2 μg/ml) in PBS (pH 7.3) was coated onto 96-well ELISA plates at 4° C. overnight. After blocking for 1 hour with 1% BSA in PBS, mAb 33D2 was two-fold serial diluted from 13.33 nM and then incubated on wells at 37° C. for 1 hour. Next, horseradish peroxidase (HRP)-conjugated goat anti-rabbit, anti-mouse IgG (1:10,000 dilution) was incubated on wells at 37° C. for another hour. Subsequently, plates were washed with PBST, followed by color development and visualization using tetramethylbenzidine (TMB) as the substrate. The absorbance was read after adding stop solution (2 N $H_2SO_4$) at OD450 nm by a microplate reader. The binding affinity of mAb 33D2 to NS1 protein was depicted in FIG. 1.

Complement-Mediated Cytolysis

To analyze complement-dependent cytolysis of infected cells, HuH-7 cells ($8\times10^3$) were infected with DENV 1-4 (multiplicity of infection=5) for 48 hours. Cells were washed with PBS, and then incubated with PBS (serving as the negative control) or 56° C. heat-inactivated antibody (i.e., control mouse IgG (designated as cmIgG), mAb 33D2, or mAb 2E8 (serving as the positive control)) as indicated (50 μg/ml) with or without Low-Tox-M rabbit complement (1:20 dilution) containing 2% FBS phenol red-free medium at 37° C. for 4-6 hours. Then, 50 μl of supernatants were collected and mixed with 50 μl of CYTOTOX 96® substrate Reagent in each well. The detection for the release of lactate dehydrogenase (LDH) were analyzed at the absorbance of 490 nm.

To determine the cytolysis by FFA, HuH-7 cells were infected with DENVs (serotype 1-4, moi=5) or mock infection for 24 hour. After 24 hours post-infection, cells were incubated with either PBS (serving as the negative control), control mouse IgG (designated as cmIgG), mAb 33D2 or mAb 2E8 (50 μg/ml, serving as the positive control) with complement (1:20 dilution) for 4-6 hours at 37° C. After refilling fresh medium for another indicated time, the infectious virus in supernatant were collected and analyzed by FFA.

Figure 4A:
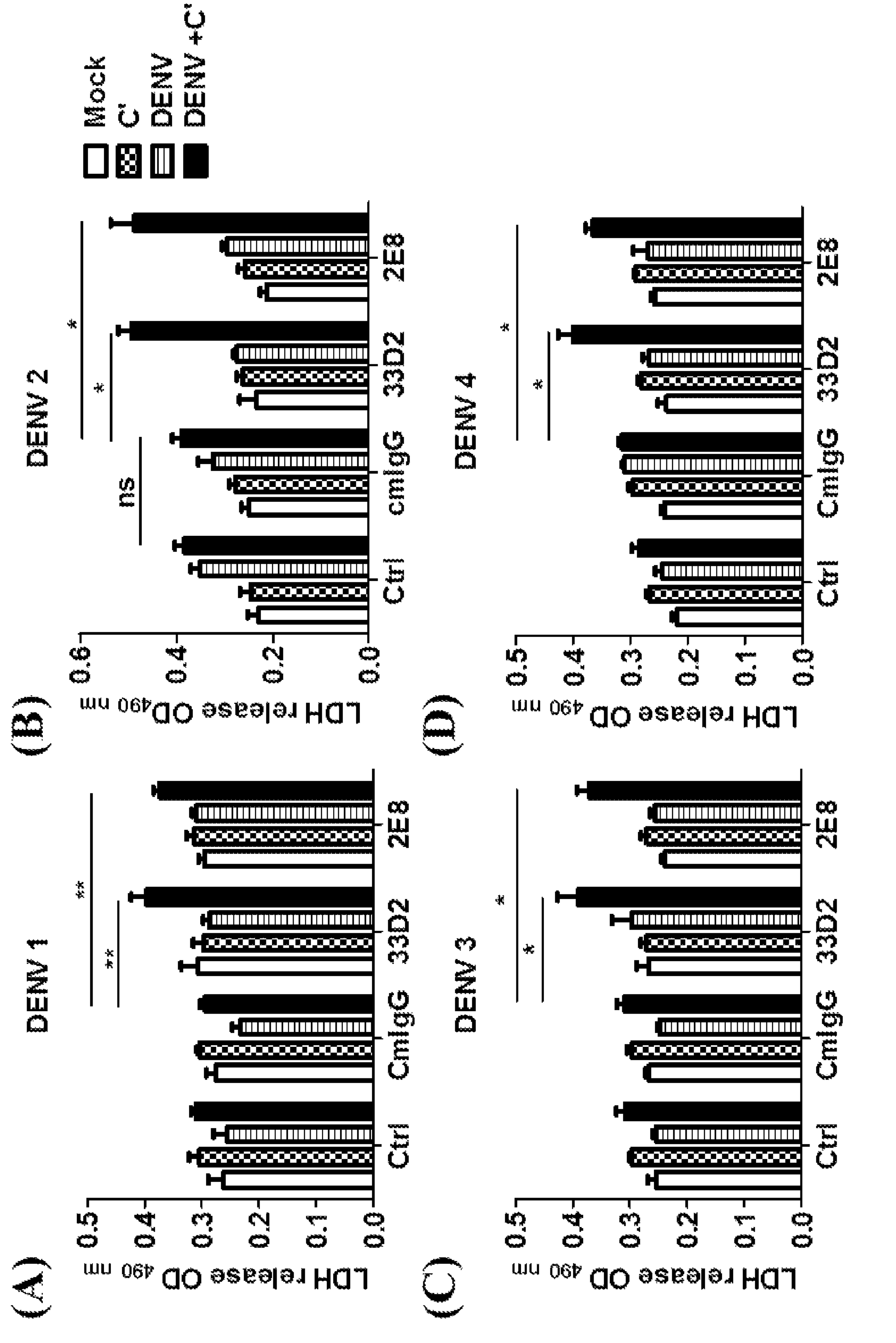
FIGS. 4A and 4B are the histogram and line chart respectively depicting that the present anti-DENV antibody 33D2 restricts viral propagation via complement-mediated lysis of DENV-infected cells, in which the lysis is measured by lactate dehydrogenase (LDH) release assay (FIG. 4A, panel A: DENV 1 infection, panel B: DENV 2 infection, panel C: DENV 3 infection, panel D: DENV 4 infection), or focus-forming units assay (FFA, FIG. 4B) according to one embodiment of the present disclosure.
Figure 4B:
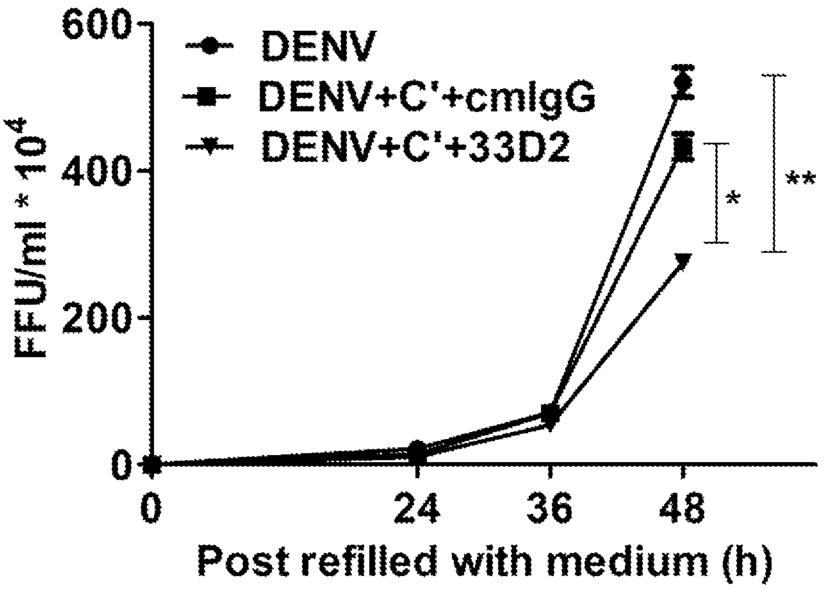

The analysis results of LDH and FFA were respectively depicted in FIGS. 4A and 4B.

Complement-Independent Inhibition

HuH-7 were infected with DENV2 (moi=2) for 12 hours, followed by incubation with either PBS, cmIg, mAb DN5C6 (another anti-NS1 mAb), mAb 33D2 or heated denatured mAb 33D2 (50 μg/ml) for another 24 hours. The supernatants containing infectious virus were used to determined viral titer by FFA. The result was depicted in FIG. 5A.

Alternatively, HuH-7 cells were infected with DENV 2 (moi=2) for 12 hours, and incubated with different doses of either cmIg or mAb 33D2. The supernatants containing infectious virus were used to determined viral titer by FFA. The treated cells were incubated with MTT reagent and cells viability was determined by MTT assay. The result was depicted in FIG. 5B.

To determine the vial titers of different DENV serotypes, HuH-7 cells were respectively infected with DENV serotypes 1-4 (moi=2) for 12 hours, followed by incubation with either PBS, cmIg, mAb DN5C6 (another anti-NS1 mAb) and different doses sof mAb 33D2. The supernatants containing infectious virus were used to determined viral titer by FFA. The result was depicted in FIG. 5C.

Hematoxylin and Eosin Staining (H&E Stain) and Immunohistochemistry (IHC)

Fresh mice skins were fixed with 4% formalin and embedded with paraffin. For histopathology analysis, tissue sections were stained with H&E. For immunohistochemistry staining, the slides were blocked and incubated with anti-NS3 antibody at 4° C. overnight. After washing with PBS, the slides were incubated with HRP-labeled secondary antibody for 30 minutes at room temperature, and then loaded onto 3,3'-diaminobenzidine (DAB) or HRP green mixed reagent for 1-5 minutes. Hematoxylin counterstain was applied for 2 minutes. The quantification of DAB staining was determined by software.

Evaluation of Cross Reaction of mAb 33D2

For cross reaction of mAb 33D2 analysis, human endothelial cells (HUVECs) and human platelets were directly stained with different dose of mAb 33D2 (2, 5, 25 μg/ml) for 1 hour, followed by staining of Alexa 488-conjugated secondary antibodies. Detection and analysis were performed using a flow cytometer. The quantification was analyzed by a software. The cross reaction between mAb 33D2 and HUVECs was depicted in FIG. 3A, and the cross reaction between mAb 33D2 and platelets was depicted in FIG. 3B.

For coagulation factors cross reactivity analysis, 50 μl of NS1, plasminogen, thrombin or BSA (2 μg/ml) in PBS (pH 7.3) were coated onto 96-well ELISA plates at 4° C. overnight. After blocking for 1 hour with 1% BSA in PBS, mAb 33D2 was two-fold serial diluted from 2 μg/ml, which were incubated on wells at 37° C. for 1 hour. Next, HRP-conjugated anti-mouse IgG (1:10,000 dilution) were incubated on wells at 37° C. for another hour. Subsequently, plates were washed with PBST, followed by color development and visualization using TMB as the substrate. The absorbance was read after adding stop solution at OD450 nm by a microplate reader. The cross reaction between mAb 33D2 and coagulated factors was depicted in FIG. 3C.

Animals

BALB/C mice obtained from Laboratory Animal Center of National Cheng Kung University (NCKU) were maintained in a 12 hour light/dark cycle with food and water provided ad libitum.

For the purpose of evaluating the therapeutic effect of mAb 33D2 in mice, four serotypes of DENVs ($2\times10^8$ PFU/mouse) or medium control were inoculated intradermally (i.d.) into C3H/HeN mice. One injection of PBS (mock), cmIgG (100 μg/mouse), or mAb 33D2 (100 μg/mouse) were inoculated i.p. one day after virus challenge. Three days after challenge, the bleeding time was determined, and the results were depicted in FIG. 6A. Fresh skin samples from mice were removed to observe the local hemorrhage, and the data was shown in FIGS. 6B and 6C. H&E staining were performed to analyze the local skin hemorrhage in the skin lesions, and the data was illustrated in FIG. 6B. The expression level of DENV NS3 protein was analyzed by IHC staining and quantified by Image J to analyze local DENV replication.

Example 1 Production and Characterization of Monoclonal Antibody (mAb)

To generate mouse mAbs, five to six-week-old BALB/c mice were immunized intraperitoneally with 50 μg insect cell-derived DENV 2 NS1 generated from drosophila by the general process of immunization. In brief, each BALB/C mice (6-8 weeks old) was intraperitoneally primed with a mixture of FCA and 25 μg DENV NS1 antigen (SEQ ID NO: 11). Two weeks later, each vaccine-primed mice was intraperitoneally boosted 2 times with the mixture comprising FIA and 25 μg of the same antigen (SEQ ID NO: 11). Three days later, the immunized mice were sacrificed, and the splenic cells isolated therefrom were immediately fused with mouse myeloma cells. The fused cells were then diluted and sequentially cultured in HAT and HT medium so as to produce hybridoma cells. Each hybridoma cells were cultured independently, and the supernatant of in each cultured wells was collected and examined for the antibody titers to the antigen comprising the amino acid sequence of "YKDWSEWGKAC" (SEQ ID NO: 12) by ELISA assay. The hybridoma exhibiting the highest specificity to the antigen was selected, and the monoclonal antibody produced therefrom was designated as mAb 33D2. The serotype of mAb 33D2 was determined by ELISA mouse mAb isotyping Kit, and the data was summarized in Table 1.

TABLE 1

| Serotype of mAb 33D2 | |
|---|---|
| Clone name | 33D2 |
| Isotype strain | Murine IgG |
| Subclass | IgG 2a |
| Light chain | Kappa light chain |

Example 2 Protective Effect of mAb 33D2 on DENV Infection In Vitro 2.1 mAb 33D2 Recognizes Four Serotypes of DENV NS1 and DENV-Infected Cells Since just few epitopes exposed outward of NS1 (either the membrane-associated NS1 or the secreted NS1 in circulation), it is difficult to find ideal antibodies against all serotypes of NS1. According to the structure-based study, disordered loop region of DENV NS1 wing domain is a promising region, which covered a highly conserved region among four serotypes of NS1. In addition, it is hypothesized to expose on the outward of NS1.

The binding affinity between the mAb 33D2 and the NS1 protein was determined by indirect ELISA assay, and the result was illustrated in FIG. 1.

Figure 2:
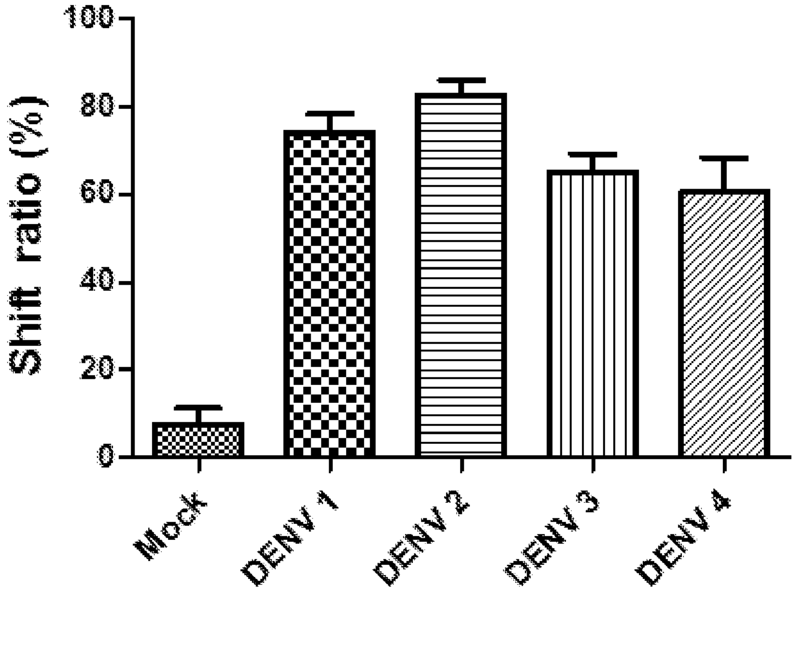
FIG. 2 is the result of flow cytometry depicting the binding affinity between the present anti-DENV antibody 33D2 and the NS1 protein on DENV serotype 1, 2, 3 or 4-infected cells according to another embodiment of the present disclosure.

According to the results of western blotting, the mAb 33D2 recognized four serotypes of commercial native NS1, but not the bovine serum albumin (BSA) (data not shown). The data of flow cytometry further confirmed that the mAb 33D2 recognized the NS1 protein expressed on the surface of cells respectively infected by DENV serotype 1, 2, 3 and 4 (FIG. 2).

Taken together, these data indicated that the mAb 33D2 recognized four serotypes of DENV (i.e., serotypes 1, 2, 3 and 4 of DENV).

2.2 mAb 33D2 does not Cross React with Host Proteins and/or Cells

It has been reported that some NS1-elicited antibodies would cross react with either human endothelial cells, human platelets, or coagulation factors, and further aggravated DHF. Accordingly, the possibility of mAb 33D2 crossed react with any of the host proteins was examined in this example.

Figure 3A:
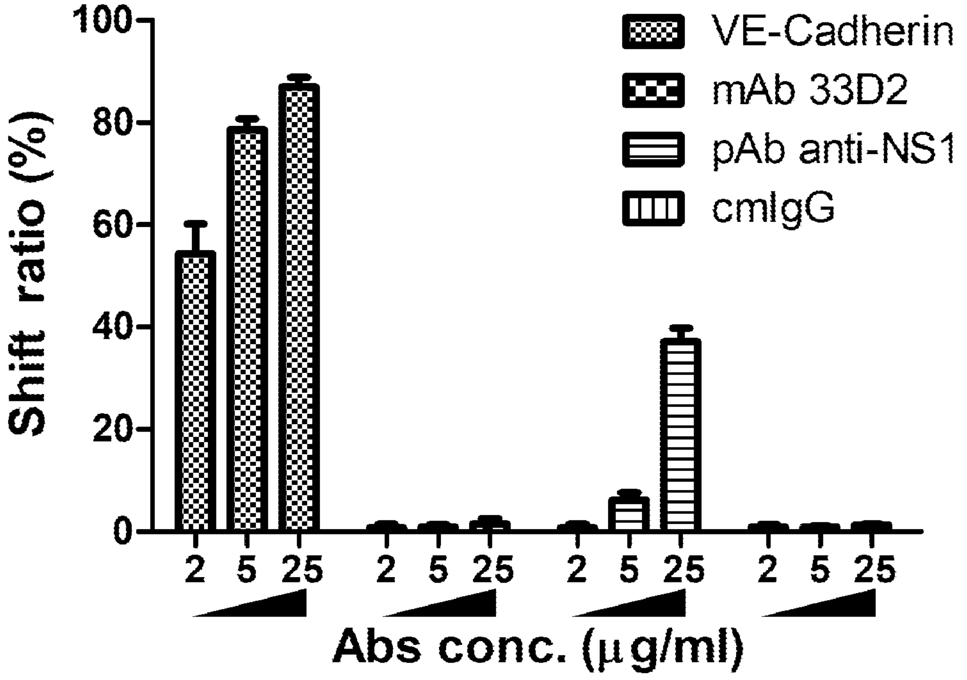
FIGS. 3A-3C are the results of flow cytometry and ELISA respectively depicting that the present anti-DENV antibody 33D2 would not cross react with the human endothelial cells (HUVECs, FIG. 3A; analyzed by flow cytometry), platelets (FIG. 3B; analyzed by flow cytometry) and coagulation factors (FIG. 3C; analyzed by ELISA) according to still another embodiment of the present disclosure.
Figure 3B:
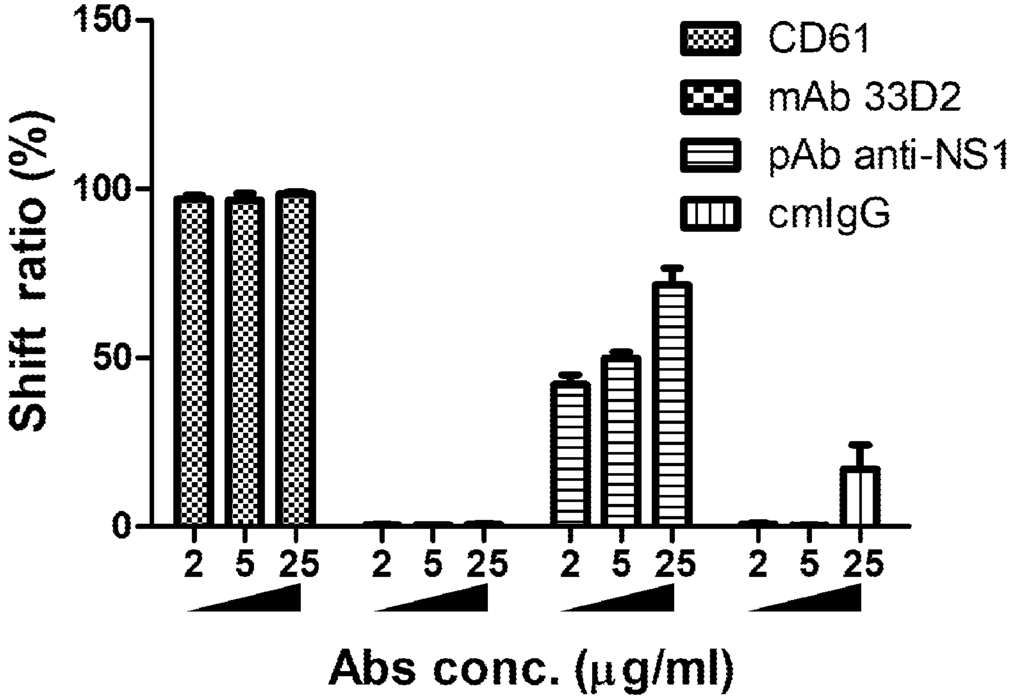
Figure 3C:
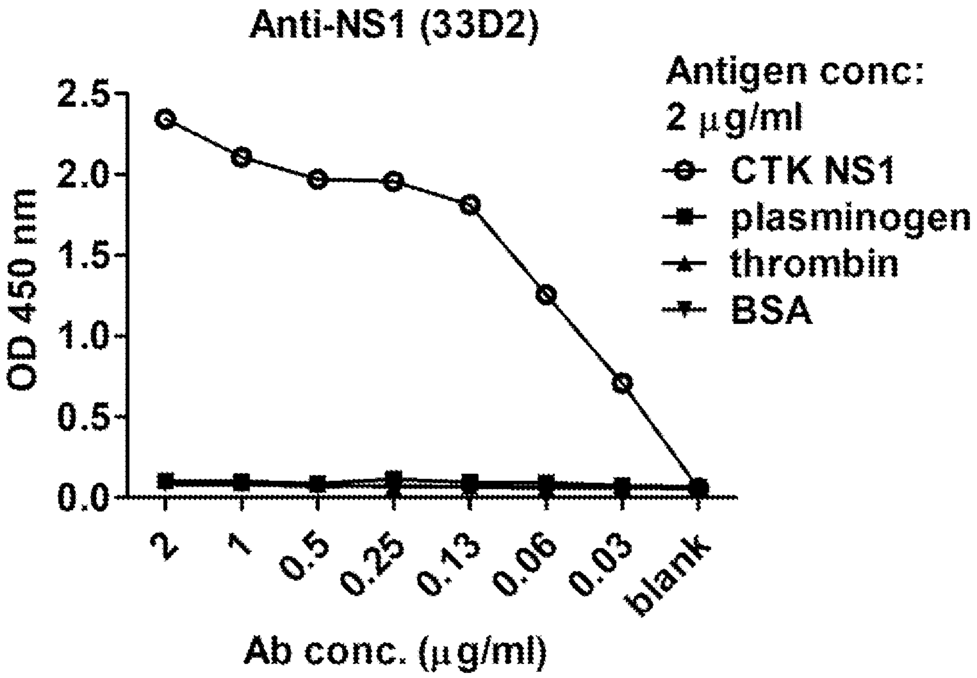

The data of flow cytometry indicated that high dosage (25 μg/ml) of anti-full length NS1 antibodies crossed react with human endothelial cells (HUVECs, FIG. 3A), platelets (FIG. 3B) and coagulation factors, including plasminogen and thrombin (FIG. 3C). By contrast, the mAb 33D2 of example 1 did not cross react with any of these cells and/or proteins (FIGS. 3A-3C).

The data demonstrated that the present anti-DENV antibody (i.e., the mAb 33D2) exhibited binding specificity to DENV.

Figure 5A:
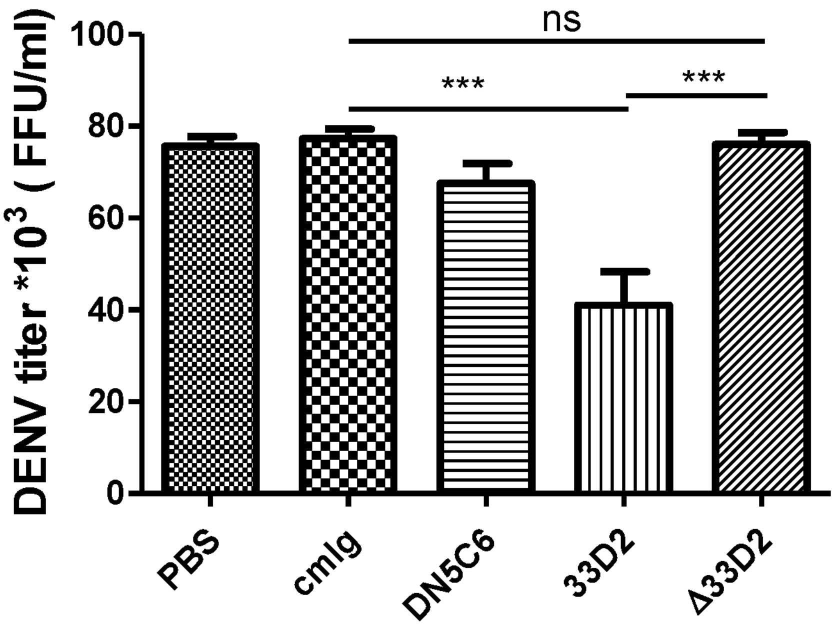
FIGS. 5A-5C are histograms respectively depicting that the present anti-DENV antibody 33D2 reduced four-serotype dengue viral titers in a complement-independent manner.
Figure 5B:
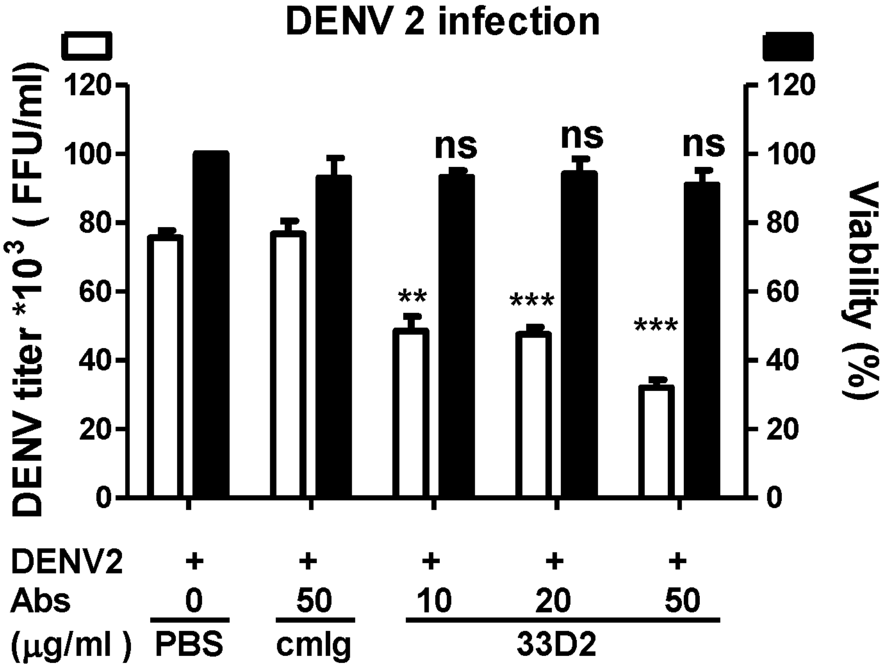
Figure 5C:
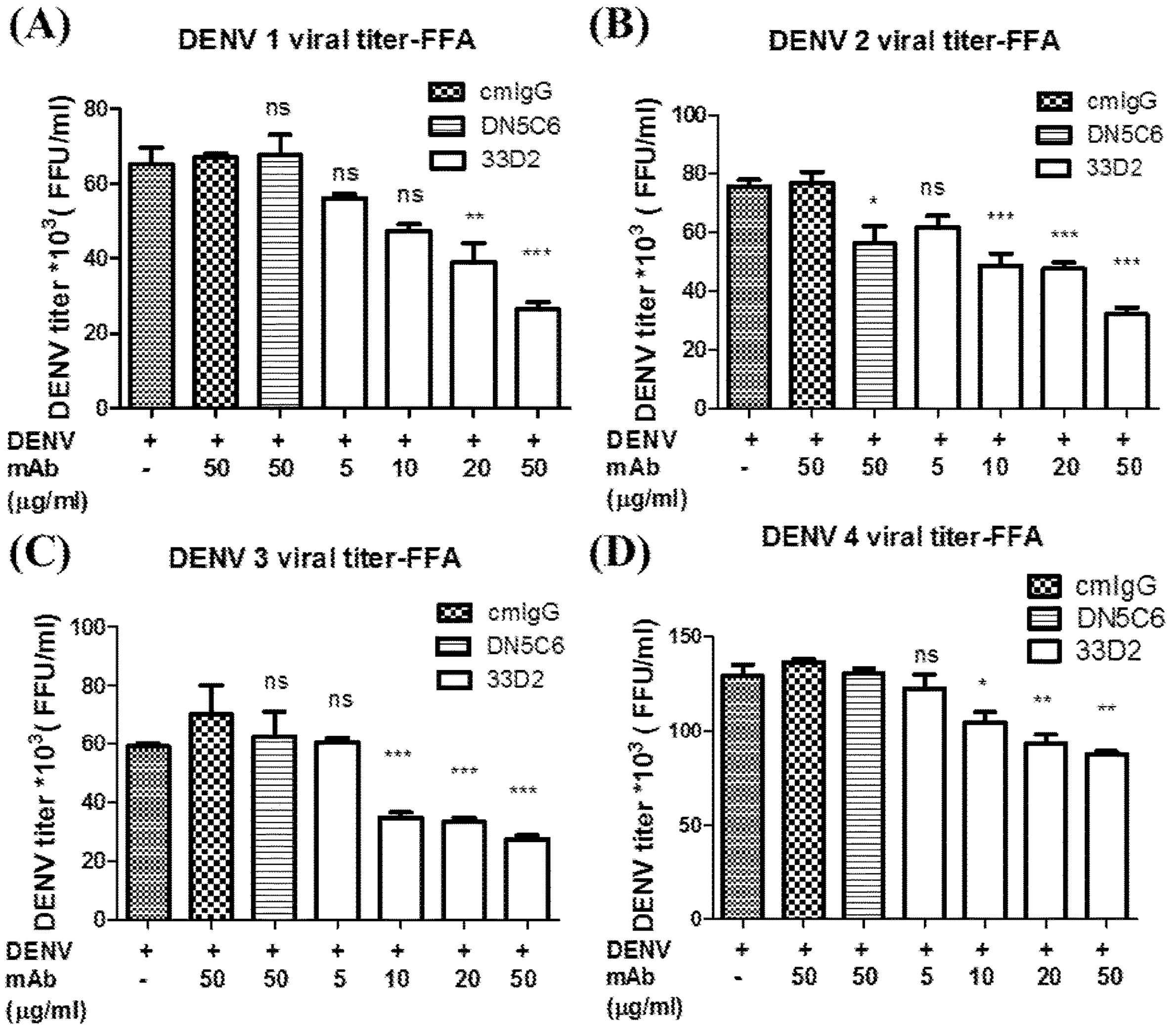

2.3 mAb 33D2 of Example 1 Reduced Viral Titer Via Complement Dependent and/or Independent Manner in Four-Serotype DENV Infection The protective mechanism of the mAb 33D2 on DENV infection was investigated in this example. The data indicated that the mAb 33D2 not only inhibited viral spreading via facilitating complement dependent cytolysis (CDC) of infected cells (FIGS. 4A and 4B), but also directly reduced viral titer in four serotype DENV infection (FIGS. 5A-5C). The analysis of FFA indicated that the mAb 33D2 significantly reduced the titer of DENV serotype 2 (FIG. 5A). The data of FIG. 5B further demonstrated that the mAb 33D2 reduced the titer of DENV serotype 2 in a dose-dependent manner. In addition to DENV serotype 2, the mAb 33D2 also exhibited inhibitory effect on DENV serotype 1, 3 and 4 (FIG. 5C).

Example 3 mAb 33D2 Provides Passive Protection Against DENV Infection in Mice The biological activity of the mAb 33D2 was examined in this example, and the data were respectively illustrated in FIGS. 6A-6E.

Figure 6A:
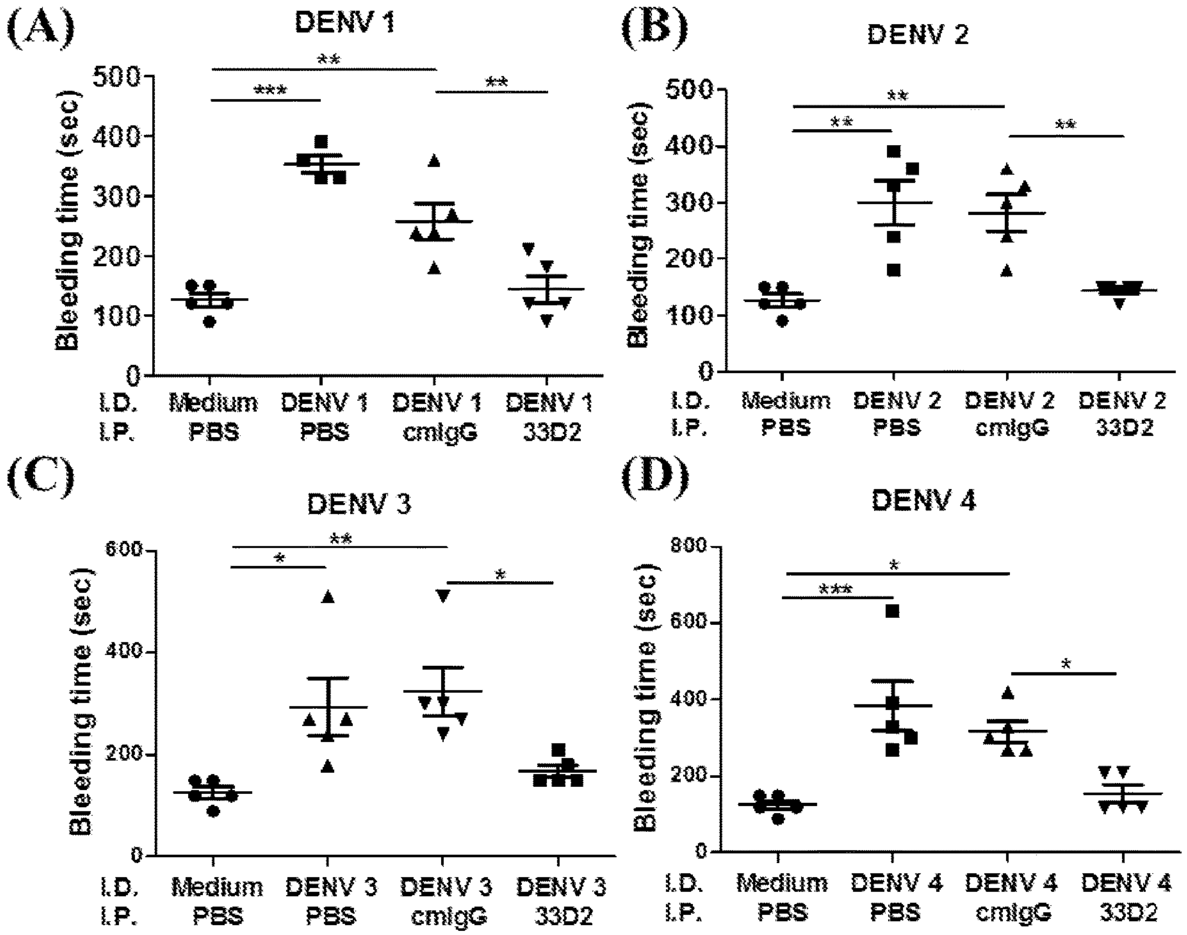
FIGS. 6A-6E are the results respectively depicting the bleeding time (FIG. 6A, in which panels A-D respectively represent DENVs 1-4 infection), the local hemorrhage (FIGS. 6B and 6C, in which panels A-D of FIG. 6C respectively represent DENVs 1-4 infection), the RBC extravasation (FIG. 6D; arrows indicate hemorrhage in the skin lesions) and the NS3 expression (FIG. 6E) of DENV-infected mice according to one embodiment of the present disclosure. Scale bar represents 10 μm.
Figure 6B:
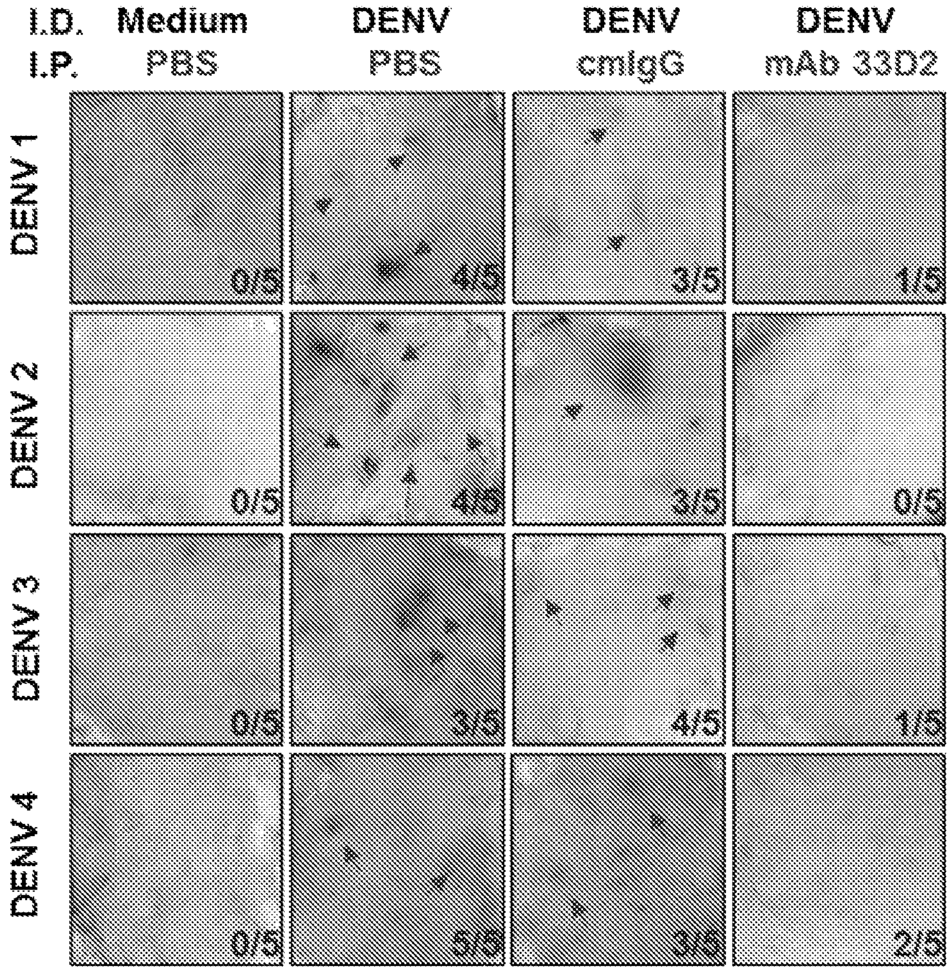
Figure 6C:
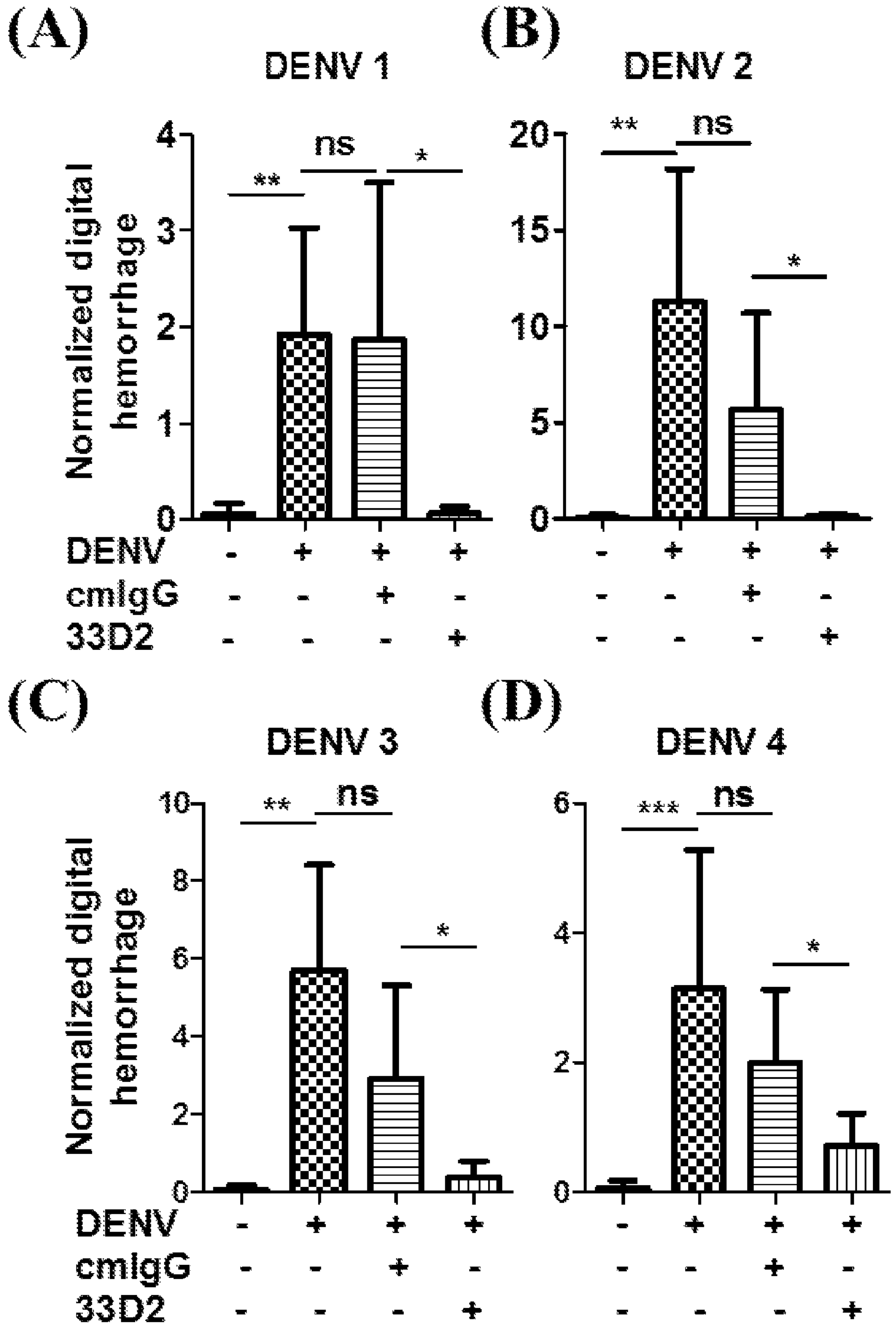
Figure 6D:
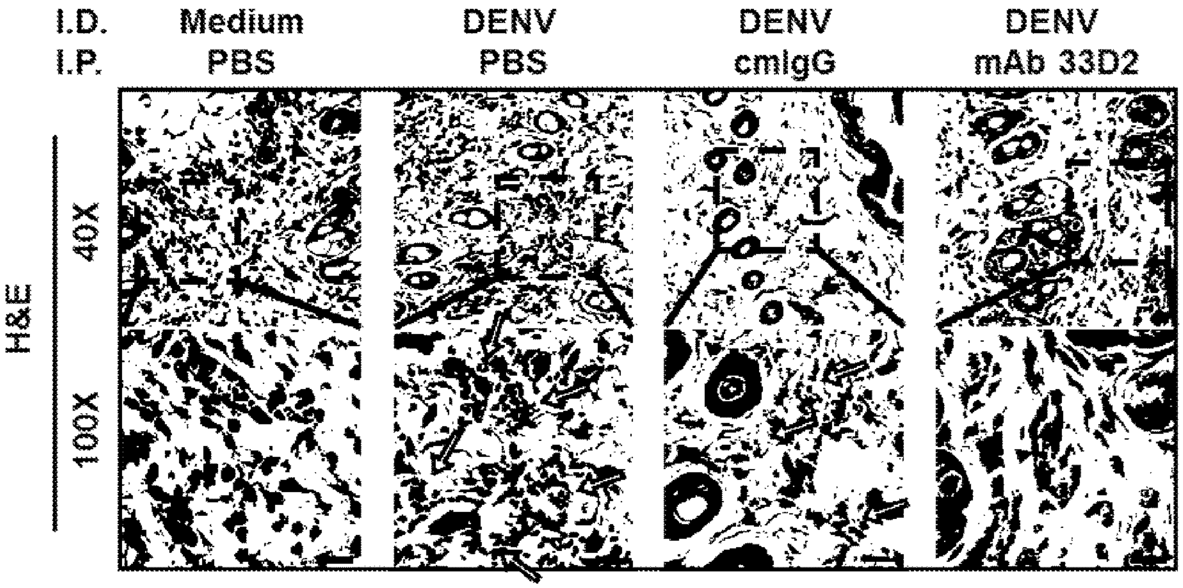

3.1 Passive Administration of mAb 33D2 Attenuated DENV-Induced Prolonged Bleeding in Mice The therapeutic effect of mAb 33D2 in vivo was investigated by use of a DENV-induced hemorrhagic mice model. Briefly, $2\times10^8$ DENVs were intradermally inoculated in the back of mice. 24 hours later, the mAb 33D2 (100 μg/ml per mouse) were given intraperitoneally to each mice inoculated with DENVs. The bleeding time (tail vein cut) in each mice was determined on day 3. The result demonstrated that DENV (i.e., DENV serotype 1, 2, 3, or 4) infection prolonged the bleeding time in mice (FIG. 6A, panels A-D). Compared to the control group (cmIg treated mice), the treatment of mAb 33D2 reduced the bleeding time in DENV-infected mouse (FIG. 6A, panels A-D).

Figure 6E:
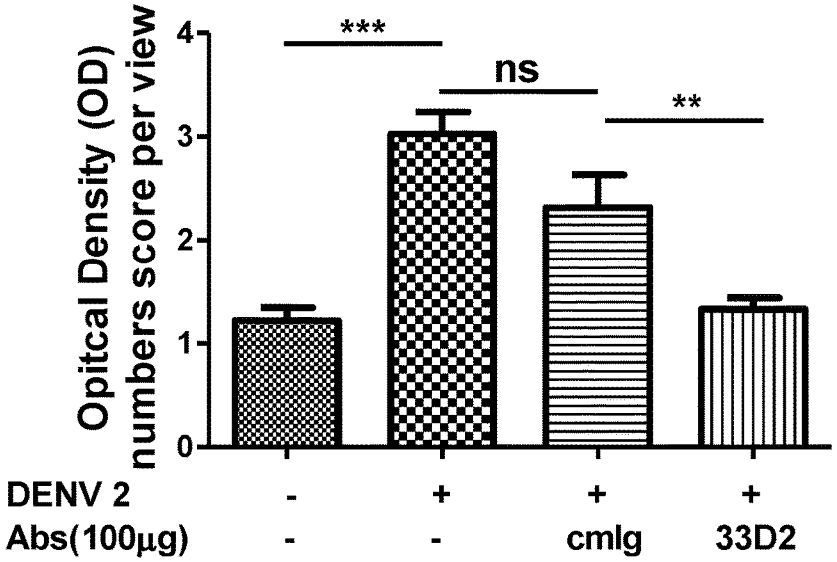

3.2 Passive Administration of mAb 33D2 Mitigated DENV-Induced Local Hemorrhage, RBC Extravasation, and DENV NS3 Expression in Mice To analyze the DENV pathology, the local hemorrhage in fresh skin lesion and extravasation of RBC in mice skin were respectively analyzed by H&E staining. Moreover, the local replication of DENV, NS3 expression, was also evaluated by IHC staining. Compared to the control group (cmIg treated mice), mAb 33D2 treated mice exhibited less local hemorrhage, RBC extravasation, and NS3 expression (FIGS. 6B-6E). Specifically, the photographs of FIG. 6B indicated that DENV (including DENV serotypes 1, 2, 3 and 4) infection caused local hemorrhage (as indicated by arrows in FIG. 6B), and the administration of mAb 33D2 obviously reduced the degree of DENV-caused local hemorrhage. The quantification results confirmed the inhibitory effect of mAb 33D2 on DENV-caused local hemorrhage (FIG. 6C, panel A: DENV 1 infection, panel B: DENV 2 infection, panel C: DENV 3 infection, panel D: DENV 4 infection). The present study also demonstrated that the mAb 33D2 obviously decreased the levels of DENV-caused RBC extravasation (FIG. 6D, the hemorrhage in the skin lesion was indicated by arrows) and NS3 expression (FIG. 6E).

In conclusion, the present invention provides a novel antibody 33D2 that exhibits binding affinity and specificity to DENV, including DENV serotypes 1, 2, 3 and 4. The present antibody would not cross react with host protein and cell, such as endothelial cells, platelets and coagulation factors. Accordingly, the present antibody may provide a potential means to efficiently treating DENV infection in a subject.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating a dengue virus infection in a subject comprising administering to the subject an effective amount of an antibody, wherein the antibody comprises a heavy chain variable region comprising amino acid sequences of SEQ ID NO: 1, SEQ ID NO: 2 and SEQ ID NO: 3; and, a light chain variable region comprising amino acid sequences of SEQ ID NO: 5, SEQ ID NO: 6 and SEQ ID NO: 7.

2. The method of claim 1, wherein the effective amount is about 1 μg/Kg to 100 mg/Kg.

3. The method of claim 2, wherein the effective amount is about 10 μg/Kg to 10 mg/Kg.

4. The method of claim 3, wherein the effective amount is about 0.1 mg/Kg to 1 mg/Kg.

5. The method of claim 1, wherein the subject is a human.

6. The method of claim 1, wherein the dengue virus is dengue virus serotype 1, 2, 3 or 4.

7. The method of claim 1, wherein the heavy chain variable region of the antibody has an amino acid sequence at least 85% identical to the sequence of SEQ ID NO: 4, and the light chain variable region of the antibody has an amino acid sequence at least 85% identical to the sequence of SEQ ID NO: 8.

8. The method of claim 7, wherein the heavy chain variable region of the antibody has the amino acid sequence of SEQ ID NO: 4, and the light chain variable region of the antibody has the amino acid sequence of SEQ ID NO: 8.

* * * * *

SEQUENCE LISTING

```
<160> NUMBER OF SEQ ID NOS: 18

<210> SEQ ID NO 1
<211> LENGTH: 11
<212> TYPE: PRT
<213> ORGANISM: Artificial Sequence
<220> FEATURE:
<223> OTHER INFORMATION: synthesized-CDRH1

<400> SEQUENCE: 1

Gly Tyr Ser Ile Thr Ser Asp Tyr Ala Trp Asn
1               5                   10


<210> SEQ ID NO 2
```

-continued

<211> LENGTH: 16
<212> TYPE: PRT
<213> ORGANISM: Artificial Sequence
<220> FEATURE:
<223> OTHER INFORMATION: synthesized-CDRH2

<400> SEQUENCE: 2

```
Phe Ile Ser Tyr Ser Gly Ser Ala Arg Tyr Asn Pro Ser Leu Ile Ser
1               5                   10                  15
```

<210> SEQ ID NO 3
<211> LENGTH: 11
<212> TYPE: PRT
<213> ORGANISM: Artificial Sequence
<220> FEATURE:
<223> OTHER INFORMATION: synthesized-CDRH3

<400> SEQUENCE: 3

```
Ala Arg Val Glu Arg Leu Gly Tyr Phe Asp Val
1               5                   10
```

<210> SEQ ID NO 4
<211> LENGTH: 118
<212> TYPE: PRT
<213> ORGANISM: Artificial Sequence
<220> FEATURE:
<223> OTHER INFORMATION: synthesized-VH chain

<400> SEQUENCE: 4

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Phe Ile Ser Tyr Ser Gly Ser Ala Arg Tyr Asn Pro Ser Leu
    50                  55                  60

Ile Ser Arg Thr Ser Ile Thr Arg Asp Thr Ser Lys Asn Gln Phe Phe
65                  70                  75                  80

Leu His Leu Asn Ser Val Thr Thr Glu Asp Thr Ala Ile Tyr Tyr Cys
                85                  90                  95

Ala Arg Val Glu Arg Leu Gly Tyr Phe Asp Val Trp Gly Ala Gly Thr
            100                 105                 110

Thr Val Thr Val Ser Ser
        115
```

<210> SEQ ID NO 5
<211> LENGTH: 15
<212> TYPE: PRT
<213> ORGANISM: Artificial Sequence
<220> FEATURE:
<223> OTHER INFORMATION: synthesized-CDRL1

<400> SEQUENCE: 5

```
Lys Ala Ser Gln Ser Val Asp Tyr Asp Gly Asp Ser Tyr Met His
1               5                   10                  15
```

<210> SEQ ID NO 6
<211> LENGTH: 7
<212> TYPE: PRT
<213> ORGANISM: Artificial Sequence
<220> FEATURE:
<223> OTHER INFORMATION: synthesized-CDRL2

-continued

<400> SEQUENCE: 6

Ala Ala Ser Asn Leu Glu Ser
1 5

<210> SEQ ID NO 7
<211> LENGTH: 8
<212> TYPE: PRT
<213> ORGANISM: Artificial Sequence
<220> FEATURE:
<223> OTHER INFORMATION: synthesized-CDRL3

<400> SEQUENCE: 7

Gln Gln Ser Asn Glu Asp Pro Thr
1 5

<210> SEQ ID NO 8
<211> LENGTH: 111
<212> TYPE: PRT
<213> ORGANISM: Artificial Sequence
<220> FEATURE:
<223> OTHER INFORMATION: synthesized-VL chain

<400> SEQUENCE: 8

```
Asp Ile Val Leu Thr Gln Ser Pro Ala Ser Leu Ala Val Ser Leu Gly
1               5                   10                  15

Gln Arg Ala Ser Ile Ser Cys Lys Ala Ser Gln Ser Val Asp Tyr Asp
            20                  25                  30

Gly Asp Ser Tyr Met His Trp Tyr Gln Gln Lys Pro Gly Gln Pro Phe
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Val Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Thr Phe Gly Gly Gly Thr Arg Leu Glu Ile Lys Arg
            100                 105                 110
```

<210> SEQ ID NO 9
<211> LENGTH: 354
<212> TYPE: DNA
<213> ORGANISM: Artificial Sequence
<220> FEATURE:
<223> OTHER INFORMATION: synthesized-VH chain

<400> SEQUENCE: 9

```
gatgtgcagc ttcaggagtc gggacctggc ctggtgaaac cttctcagtc tctgtccctc      60

acctgcactg tcactggcta ctcaatcacc agtgattatg cctggaactg gatccggcag     120

tttccaggaa acaagctgga gtggatgggc ttcataagtt acagtggtag cgctaggtac     180

aatccatctc tcataagtcg aacctctatc actcgagaca catccaagaa ccagttcttc     240

ctgcacttga attctgtgac tactgaggac acagccatat attactgtgc gagagtggaa     300

cggctagggt acttcgatgt ctggggcgca gggaccacgg tcaccgtctc ctca           354
```

<210> SEQ ID NO 10
<211> LENGTH: 333
<212> TYPE: DNA
<213> ORGANISM: Artificial Sequence
<220> FEATURE:
<223> OTHER INFORMATION: synthesized-VL chain -continued

<400> SEQUENCE: 10
gacattgtgc tgacccaatc tccagcttct ttggctgtgt ctctagggca gagggcctcc 60
atctcctgca aggccagcca aagtgttgat tatgatggtg atagttatat gcactggtac 120
caacagaaac caggacagcc attcaaactc ctcatctatg ctgcatccaa tctagaatct 180
gggatcccag ccaggtttag tggcagtggg tctgggacag tcttcaccct caacatccat 240
cctgtggagg aggaggatgc tgcaacctat tactgtcagc aaagtaatga ggatccgacg 300
ttcggtggag gcaccaggct ggaaatcaaa cgg 333

<210> SEQ ID NO 11
<211> LENGTH: 354
<212> TYPE: PRT
<213> ORGANISM: Artificial Sequence
<220> FEATURE:
<223> OTHER INFORMATION: synthesized-DENV NS1 antigen

<400> SEQUENCE: 11

Ser Gly Cys Val Val Ser Trp Lys Asn Lys Glu Leu Lys Cys Gly Ser
1 5 10 15

Gly Ile Phe Ile Thr Asp Asn Val His Thr Trp Thr Glu Gln Tyr Lys
20 25 30

Phe Gln Pro Glu Ser Pro Ser Lys Leu Ala Ser Ala Ile Gln Lys Ala
35 40 45

His Glu Glu Gly Ile Cys Gly Ile Arg Ser Val Thr Arg Leu Glu Asn
50 55 60

Leu Met Trp Lys Gln Ile Thr Pro Glu Leu Asn His Ile Leu Ser Glu
65 70 75 80

Asn Glu Val Lys Leu Thr Ile Met Thr Gly Asp Ile Lys Gly Ile Met
85 90 95

Gln Ala Gly Lys Arg Ser Leu Arg Pro Gln Pro Thr Glu Leu Lys Tyr
100 105 110

Ser Trp Lys Ala Trp Gly Lys Ala Lys Met Leu Ser Thr Glu Leu His
115 120 125

Asn His Thr Phe Leu Ile Asp Gly Pro Glu Thr Ala Glu Cys Pro Asn
130 135 140

Thr Asn Arg Ala Trp Asn Ser Leu Glu Val Glu Asp Tyr Gly Phe Gly
145 150 155 160

Val Phe Thr Thr Asn Ile Trp Leu Lys Leu Lys Glu Arg Gln Asp Val
165 170 175

Phe Cys Asp Ser Lys Leu Met Ser Ala Ala Ile Lys Asp Asn Arg Ala
180 185 190

Val His Ala Asp Met Gly Tyr Trp Ile Glu Ser Ala Leu Asn Asp Thr
195 200 205

Trp Lys Ile Glu Lys Ala Ser Phe Ile Glu Val Lys Ser Cys His Trp
210 215 220

Pro Lys Ser His Thr Leu Trp Ser Asn Gly Val Leu Glu Ser Glu Met
225 230 235 240

Ile Ile Pro Lys Asn Phe Ala Gly Pro Val Ser Gln His Asn Tyr Arg
245 250 255

Pro Gly Tyr His Thr Gln Thr Ala Gly Pro Trp His Leu Gly Lys Leu
260 265 270

Glu Met Asp Phe Asp Phe Cys Glu Gly Thr Thr Val Val Val Thr Glu
275 280 285

Asp Cys Gly Asn Arg Gly Pro Ser Leu Arg Thr Thr Thr Ala Ser Gly

```
    290                 295                 300

Lys Leu Ile Thr Glu Trp Cys Cys Arg Ser Cys Thr Leu Pro Pro Leu
305                 310                 315                 320

Arg Tyr Arg Gly Glu Asp Gly Cys Trp Tyr Gly Met Glu Ile Arg Pro
                325                 330                 335

Leu Lys Glu Lys Glu Glu Asn Leu Val Asn Ser Leu Val Thr Ala Gly
            340                 345                 350

His Gly


<210> SEQ ID NO 12
<211> LENGTH: 11
<212> TYPE: PRT
<213> ORGANISM: Artificial Sequence
<220> FEATURE:
<223> OTHER INFORMATION: synthesized

<400> SEQUENCE: 12

Tyr Lys Asp Trp Ser Glu Trp Gly Lys Ala Cys
1               5                   10


<210> SEQ ID NO 13
<211> LENGTH: 33
<212> TYPE: DNA
<213> ORGANISM: Artificial Sequence
<220> FEATURE:
<223> OTHER INFORMATION: synthesized-CDRH1

<400> SEQUENCE: 13

ggctactcaa tcaccagtga ttatgcctgg aac                                  33


<210> SEQ ID NO 14
<211> LENGTH: 48
<212> TYPE: DNA
<213> ORGANISM: Artificial Sequence
<220> FEATURE:
<223> OTHER INFORMATION: synthesized-CDRH2

<400> SEQUENCE: 14

ttcataagtt acagtggtag cgctaggtac aatccatctc tcataagt                  48


<210> SEQ ID NO 15
<211> LENGTH: 33
<212> TYPE: DNA
<213> ORGANISM: Artificial Sequence
<220> FEATURE:
<223> OTHER INFORMATION: synthesized-CDRH3

<400> SEQUENCE: 15

gcgagagtgg aacggctagg gtacttcgat gtc                                  33


<210> SEQ ID NO 16
<211> LENGTH: 45
<212> TYPE: PRT
<213> ORGANISM: Artificial Sequence
<220> FEATURE:
<223> OTHER INFORMATION: synthesized-CDRL1

<400> SEQUENCE: 16

Ala Ala Gly Gly Cys Cys Ala Gly Cys Cys Ala Ala Ala Gly Thr Gly
1               5                   10                  15

Thr Thr Gly Ala Thr Thr Ala Thr Gly Ala Thr Gly Gly Thr Gly Ala
            20                  25                  30

Thr Ala Gly Thr Thr Ala Thr Ala Thr Gly Cys Ala Cys
```

-continued

```
        35                  40                  45


<210> SEQ ID NO 17
<211> LENGTH: 21
<212> TYPE: DNA
<213> ORGANISM: Artificial Sequence
<220> FEATURE:
<223> OTHER INFORMATION: synthesized-CDRL2

<400> SEQUENCE: 17

gctgcatcca atctagaatc t                                              21


<210> SEQ ID NO 18
<211> LENGTH: 24
<212> TYPE: DNA
<213> ORGANISM: Artificial Sequence
<220> FEATURE:
<223> OTHER INFORMATION: synthesized-CDRL3

<400> SEQUENCE: 18

cagcaaagta atgaggatcc gacg                                           24
```